United States Patent
Lozada

(10) Patent No.: US 10,639,132 B2
(45) Date of Patent: May 5, 2020

(54) DENTAL PROSTHESIS

(71) Applicant: Italo Lozada, Brookline, MA (US)

(72) Inventor: Italo Lozada, Brookline, MA (US)

(*) Notice: Subject to any disclaimer, the term of this patent is extended or adjusted under 35 U.S.C. 154(b) by 159 days.

(21) Appl. No.: 14/485,068

(22) Filed: Sep. 12, 2014

(65) Prior Publication Data

US 2016/0074141 A1   Mar. 17, 2016

(51) Int. Cl.
| | | |
|---|---|---|
| *A61C 13/08* | (2006.01) | |
| *A61C 8/00* | (2006.01) | |
| *A61C 5/30* | (2017.01) | |
| *A61C 1/08* | (2006.01) | |
| *A61C 13/107* | (2006.01) | |
| *A61B 6/14* | (2006.01) | |
| *A61B 6/00* | (2006.01) | |

(52) U.S. Cl.
CPC .............. *A61C 13/08* (2013.01); *A61C 1/084* (2013.01); *A61C 5/30* (2017.02); *A61C 8/008* (2013.01); *A61C 8/0022* (2013.01); *A61C 8/0089* (2013.01); *A61C 13/0001* (2013.01); *A61B 6/14* (2013.01); *A61B 6/466* (2013.01)

(58) Field of Classification Search
CPC ......... A61C 8/008; A61C 1/082; A61C 1/084; A61C 1/085; A61C 8/00; A61C 8/0009; A61C 8/003–0039; A61C 8/0048; A61C 8/005; A61C 8/0068; A61C 8/0075; A61C 8/0028; A61C 2008/0084; A61C 13/08; A61C 13/0001; A61C 13/00; A61C 13/30; A61C 3/04; A61C 3/30; A61C 5/35

USPC .......................................... 433/174, 173, 72
See application file for complete search history.

(56) References Cited

U.S. PATENT DOCUMENTS

| | | | | |
|---|---|---|---|---|
| 581,335 | A | * | 4/1897 | Carr ..................... A61C 8/0022 433/174 |
| 1,340,089 | A | * | 5/1920 | Stone ................. A61C 13/2653 433/181 |
| 2,705,837 | A | | 4/1955 | Gerlach |
| 2,721,387 | A | | 10/1955 | Ashuckian |
| 3,348,311 | A | * | 10/1967 | Weissman ............. A61C 5/007 164/34 |
| 3,466,748 | A | | 9/1969 | Christensen |
| 3,590,485 | A | * | 7/1971 | Chercheve .......... A61C 8/0012 433/174 |
| 3,813,779 | A | | 6/1974 | Tosti |
| 3,928,914 | A | | 12/1975 | Kozlovsky |
| 4,268,253 | A | | 5/1981 | Gross et al. |
| 4,324,549 | A | | 4/1982 | Madray |
| 4,360,342 | A | * | 11/1982 | Salvo ..................... A61C 13/26 433/172 |
| 4,439,152 | A | * | 3/1984 | Small ...................... A61C 8/00 433/173 |

(Continued)

FOREIGN PATENT DOCUMENTS

| | | |
|---|---|---|
| EP | 0291103 | 11/1988 |
| EP | 0625030 | 11/1994 |

(Continued)

*Primary Examiner* — Alvin J Stewart
(74) *Attorney, Agent, or Firm* — Lambert Shortell & Connaughton; Gary E. Lambert; David J. Connaughton, Jr.

(57) ABSTRACT

A dental prosthesis having a guide hole formed therein. The guide hole is configured to guide a drilling for a screw, and configured to receive the screw, holding the prosthesis in place when screwed into the bone of a patient.

15 Claims, 3 Drawing Sheets

(56) References Cited

U.S. PATENT DOCUMENTS

| | | | | |
|---|---|---|---|---|
| 4,479,527 A | * | 10/1984 | Boettcher | A61C 13/26 164/34 |
| 4,744,756 A | * | 5/1988 | Ross | A61C 8/0039 433/173 |
| 4,762,492 A | * | 8/1988 | Nagai | A61C 8/001 433/174 |
| 4,772,204 A | | 9/1988 | Soederberg | |
| 4,820,157 A | * | 4/1989 | Salvo | A61C 5/007 433/180 |
| 4,832,601 A | | 5/1989 | Linden | |
| 4,850,870 A | * | 7/1989 | Lazzara | A61C 8/0048 433/173 |
| 4,854,872 A | * | 8/1989 | Detsch | A61C 8/0069 433/173 |
| 4,872,840 A | * | 10/1989 | Bori | A61C 3/16 433/173 |
| 4,988,298 A | * | 1/1991 | Lazzara | A61C 8/005 433/173 |
| 5,006,069 A | * | 4/1991 | Lazzara | A61C 8/008 433/173 |
| 5,007,834 A | * | 4/1991 | Rubinstein | A61C 8/00 433/173 |
| 5,009,596 A | * | 4/1991 | Soderberg | A61C 8/0001 433/173 |
| 5,064,373 A | * | 11/1991 | Staubli | A61C 8/0048 433/173 |
| 5,071,351 A | * | 12/1991 | Green, Jr. | A61C 8/0012 433/173 |
| 5,104,318 A | * | 4/1992 | Piche | A61C 8/0068 433/173 |
| 5,125,839 A | * | 6/1992 | Ingber | A61C 8/0001 433/169 |
| 5,180,303 A | * | 1/1993 | Hornburg | A61C 13/0003 433/173 |
| 5,195,891 A | | 4/1993 | Sulc | |
| 5,302,127 A | * | 4/1994 | Crisio, Jr. | A61C 8/0086 433/173 |
| 5,376,004 A | * | 12/1994 | Mena | A61C 8/0048 433/173 |
| 5,399,090 A | * | 3/1995 | Padros-Fradera | A61C 8/0074 433/173 |
| 5,417,568 A | * | 5/1995 | Giglio | A61C 8/005 433/172 |
| 5,453,007 A | * | 9/1995 | Wagher | A61C 8/005 433/177 |
| 5,468,150 A | * | 11/1995 | Brammann | A61K 6/083 433/173 |
| 5,496,371 A | * | 3/1996 | Eppley | A61L 27/26 623/17.18 |
| 5,503,558 A | * | 4/1996 | Clokie | A61C 8/0018 433/172 |
| 5,513,989 A | * | 5/1996 | Crisio | A61C 8/0086 433/176 |
| 5,542,847 A | * | 8/1996 | Margulies | A61C 1/084 433/173 |
| 5,556,278 A | * | 9/1996 | Meitner | A61C 1/084 433/213 |
| 5,605,457 A | * | 2/1997 | Bailey | A61C 8/005 433/173 |
| 5,636,986 A | * | 6/1997 | Pezeshkian | A61C 1/084 433/213 |
| 5,674,069 A | * | 10/1997 | Osorio | A61C 8/005 433/172 |
| 5,695,336 A | * | 12/1997 | Lazzara | A61C 8/0022 433/173 |
| 5,711,669 A | * | 1/1998 | Hurson | A61C 8/0012 433/174 |
| 5,733,122 A | * | 3/1998 | Gordon | A61C 8/005 433/172 |
| 5,785,525 A | * | 7/1998 | Weissman | A61C 8/0018 433/174 |
| 5,810,592 A | * | 9/1998 | Daftary | A61C 8/005 433/172 |
| 5,813,858 A | * | 9/1998 | Singer | A61C 8/008 433/141 |
| 5,829,977 A | * | 11/1998 | Rogers | A61C 8/005 433/172 |
| 5,833,463 A | * | 11/1998 | Hurson | A61C 8/0012 433/172 |
| 5,882,200 A | * | 3/1999 | Sutter | A61C 8/0001 433/173 |
| 5,890,902 A | * | 4/1999 | Sapian | A61C 8/0048 433/173 |
| 5,906,488 A | * | 5/1999 | Kvarnstrom | A61C 8/0089 433/116 |
| 5,906,489 A | * | 5/1999 | Khazzam | A61C 8/0022 433/173 |
| 5,915,962 A | * | 6/1999 | Rosenlicht | A61C 1/084 433/76 |
| 5,967,777 A | * | 10/1999 | Klein | A61C 1/084 433/75 |
| 5,989,029 A | * | 11/1999 | Osorio | A61C 8/005 433/173 |
| 6,120,292 A | * | 9/2000 | Buser | A61C 8/008 433/172 |
| 6,244,867 B1 | * | 6/2001 | Aravena | A61C 8/005 433/172 |
| 6,364,664 B1 | * | 4/2002 | Watanabe | A61C 8/0048 433/173 |
| 6,450,812 B1 | * | 9/2002 | Laster | A61C 1/084 433/173 |
| 6,793,491 B2 | * | 9/2004 | Klein | A61C 1/084 433/173 |
| 6,939,135 B2 | * | 9/2005 | Sapian | A61C 8/005 433/174 |
| 6,981,873 B2 | * | 1/2006 | Choi | A61C 8/0025 433/173 |
| 6,986,661 B2 | * | 1/2006 | Kim | A61C 13/225 433/181 |
| 7,175,434 B2 | * | 2/2007 | Brajnovic | A61C 8/0048 433/173 |
| 7,300,282 B2 | * | 11/2007 | Sapian | A61C 8/0057 433/169 |
| 7,429,175 B2 | * | 9/2008 | Gittelson | A61C 1/084 433/173 |
| 7,708,557 B2 | * | 5/2010 | Rubbert | A61C 5/007 433/172 |
| 7,798,812 B2 | * | 9/2010 | Last-Pollak | A61C 8/0048 433/169 |
| 7,806,685 B1 | * | 10/2010 | Grant | A61C 8/005 433/14 |
| 7,850,452 B2 | * | 12/2010 | Suttin | A61C 8/0022 433/173 |
| 8,038,440 B2 | * | 10/2011 | Swaelens | A61C 1/084 433/76 |
| 8,185,224 B2 | * | 5/2012 | Powell | A61C 8/00 433/173 |
| 8,206,153 B2 | * | 6/2012 | Suttin | A61C 8/00 433/215 |
| 8,231,386 B2 | * | 7/2012 | Hertz | A61C 8/001 433/173 |
| 8,323,022 B2 | * | 12/2012 | Yoon | A61C 13/275 433/172 |
| 8,406,909 B2 | * | 3/2013 | Yau | A61C 8/0001 433/173 |
| 8,562,344 B2 | * | 10/2013 | Grant | A61C 8/001 433/172 |
| 8,851,891 B2 | * | 10/2014 | Lomicka | A61C 8/0033 433/173 |
| 8,899,982 B2 | * | 12/2014 | Damstra | A61C 8/0012 433/174 |
| 8,920,167 B2 | * | 12/2014 | Akutsu | A61C 1/084 433/72 |
| 8,936,469 B2 | * | 1/2015 | Smith | A61C 8/005 433/201.1 |
| 9,039,414 B2 | * | 5/2015 | Bulloch | A61C 1/084 433/75 |

(56) References Cited

U.S. PATENT DOCUMENTS

| | | | |
|---|---|---|---|
| 9,504,535 B2* | 11/2016 | Haber | A61C 8/0089 |
| 9,603,680 B2* | 3/2017 | Antonini | A61C 8/005 |
| 9,872,757 B2* | 1/2018 | Kelly | A61F 2/022 |
| 10,507,081 B2* | 12/2019 | Blaisdell | A61C 8/008 |
| 2002/0028424 A1* | 3/2002 | Prestipino | A61C 8/00 433/201.1 |
| 2002/0031747 A1* | 3/2002 | Laster | A61C 1/084 433/173 |
| 2002/0039717 A1* | 4/2002 | Amber | A61C 8/0001 433/172 |
| 2002/0076673 A1* | 6/2002 | Wagner | A61C 8/005 433/173 |
| 2002/0147497 A1* | 10/2002 | Belef | A61F 2/02 623/17.12 |
| 2002/0160337 A1* | 10/2002 | Klein | A61C 1/084 433/213 |
| 2002/0177104 A1* | 11/2002 | Klein | A61C 1/084 433/173 |
| 2003/0224328 A1* | 12/2003 | Sapian | A61C 8/005 433/173 |
| 2004/0137410 A1* | 7/2004 | Phimmasone | A61C 9/002 433/213 |
| 2004/0259056 A1 | 12/2004 | Holt | |
| 2005/0142517 A1* | 6/2005 | Frysh | A61C 13/0004 433/173 |
| 2005/0143743 A1* | 6/2005 | Cigada | A61L 27/047 606/76 |
| 2005/0170311 A1* | 8/2005 | Tardieu | A61C 8/0089 433/76 |
| 2005/0202368 A1* | 9/2005 | Ganley | A61C 8/005 433/173 |
| 2006/0014120 A1* | 1/2006 | Sapian | A61C 8/0057 433/173 |
| 2006/0040234 A1* | 2/2006 | Posca | A61C 13/2255 433/177 |
| 2006/0093992 A1* | 5/2006 | Wen | A61C 9/002 433/213 |
| 2006/0127848 A1* | 6/2006 | Sogo | A61C 1/084 433/173 |
| 2006/0141418 A1* | 6/2006 | Heo | A61C 8/0048 433/173 |
| 2006/0141419 A1* | 6/2006 | Heo | A61C 8/0048 433/201.1 |
| 2006/0166169 A1* | 7/2006 | Dawood | A61B 17/666 433/174 |
| 2007/0111156 A1* | 5/2007 | Gittelson | A61C 1/084 433/72 |
| 2008/0057467 A1* | 3/2008 | Gittelson | A61C 1/084 433/72 |
| 2008/0124676 A1* | 5/2008 | Marotta | A61C 1/084 433/174 |
| 2008/0206708 A1* | 8/2008 | Kwon | A61C 13/003 433/172 |
| 2008/0254413 A1* | 10/2008 | Gampert | A61C 8/0069 433/223 |
| 2008/0274440 A1* | 11/2008 | Smith | A61C 8/005 433/174 |
| 2009/0130631 A1* | 5/2009 | Chen | A61C 8/0022 433/174 |
| 2009/0226857 A1* | 9/2009 | Grant | A61C 8/0048 433/174 |
| 2009/0246733 A1 | 10/2009 | Auderset et al. | |
| 2009/0269718 A1* | 10/2009 | Duncan | A61C 1/084 433/174 |
| 2009/0286201 A1* | 11/2009 | Choe | A61C 1/084 433/165 |
| 2009/0286202 A1* | 11/2009 | Ford | A61C 8/0016 433/174 |
| 2010/0035209 A1* | 2/2010 | Jang | A61C 13/273 433/194 |
| 2010/0119995 A1* | 5/2010 | Grant | A61C 8/005 433/174 |
| 2010/0159419 A1* | 6/2010 | Grant | A61C 8/001 433/174 |
| 2010/0173260 A1* | 7/2010 | Sogo | A61C 1/084 433/75 |
| 2010/0240000 A1* | 9/2010 | Yau | A61C 1/084 433/37 |
| 2010/0297583 A1* | 11/2010 | Benzon | A61C 8/0048 433/174 |
| 2011/0033815 A1* | 2/2011 | Stonisch | A61C 19/10 433/24 |
| 2011/0065064 A1* | 3/2011 | Kahdemann | A61C 8/0012 433/174 |
| 2011/0129792 A1* | 6/2011 | Berckmans, III | A61C 1/084 433/72 |
| 2011/0143307 A1* | 6/2011 | Takebayashi | A61B 6/12 433/74 |
| 2011/0151408 A1* | 6/2011 | Grant | A61C 8/001 433/174 |
| 2011/0183289 A1* | 7/2011 | Powell | A61C 8/00 433/173 |
| 2011/0207084 A1* | 8/2011 | Kaigler, Sr. | A61B 17/663 433/174 |
| 2011/0229854 A1* | 9/2011 | Fischler | A61C 8/005 433/174 |
| 2011/0244425 A1* | 10/2011 | Wiener | A61C 8/005 433/173 |
| 2011/0287385 A1* | 11/2011 | Artal Arruga | A61C 8/0086 433/174 |
| 2012/0065756 A1* | 3/2012 | Rubbert | A61C 8/0006 700/98 |
| 2012/0077149 A1* | 3/2012 | Ospelt | A61C 8/005 433/173 |
| 2012/0189985 A1* | 7/2012 | Iglesias | A61C 8/0048 433/174 |
| 2012/0196250 A1* | 8/2012 | Grant | A61C 8/0069 433/174 |
| 2012/0202170 A1* | 8/2012 | Johnson | A61C 8/005 433/173 |
| 2012/0251974 A1* | 10/2012 | Katz | A61C 1/084 433/75 |
| 2013/0011813 A1* | 1/2013 | Alvarez Garcia | A61C 1/084 433/173 |
| 2013/0017510 A1* | 1/2013 | Rudo | A61C 5/007 433/172 |
| 2013/0022942 A1* | 1/2013 | Zadeh | A61C 8/0024 433/174 |
| 2013/0023888 A1* | 1/2013 | Choi | A61C 1/084 606/96 |
| 2013/0101962 A1* | 4/2013 | Howe | A61C 9/0053 433/191 |
| 2013/0171587 A1* | 7/2013 | Akutsu | A61C 1/084 433/173 |
| 2013/0177872 A1* | 7/2013 | Blaisdell | A61C 8/008 433/173 |
| 2013/0260337 A1* | 10/2013 | Duncan | A61C 8/0089 433/174 |
| 2013/0269165 A1* | 10/2013 | Marotta | A61C 8/0001 29/428 |
| 2014/0017632 A1* | 1/2014 | Ryu | A61C 8/0048 433/173 |
| 2014/0057227 A1* | 2/2014 | Cheng | A61C 8/009 433/173 |
| 2014/0178835 A1* | 6/2014 | Lin | A61C 8/0001 433/173 |
| 2014/0178836 A1* | 6/2014 | Haus | A61C 8/0068 433/173 |
| 2014/0205969 A1* | 7/2014 | Marlin | A61C 8/008 433/173 |
| 2014/0302460 A1* | 10/2014 | Cramer Von Clausbruch | A61C 8/0051 433/201.1 |
| 2014/0349250 A1* | 11/2014 | Elsner | A61C 8/005 433/174 |
| 2015/0010883 A1* | 1/2015 | Garcia Saban | A61C 13/0018 433/173 |

(56) References Cited

U.S. PATENT DOCUMENTS

| | | | |
|---|---|---|---|
| 2015/0017603 A1* | 1/2015 | Antonini | A61C 8/005 433/173 |
| 2015/0044635 A1* | 2/2015 | Wang | A61C 8/005 433/173 |
| 2015/0099238 A1* | 4/2015 | Chesler | A61C 13/30 433/165 |
| 2015/0157426 A1* | 6/2015 | Choi | A61C 8/006 433/174 |
| 2015/0216635 A1* | 8/2015 | Schweiger | A61K 6/0005 433/173 |
| 2015/0351875 A1* | 12/2015 | Mielecke | A61C 8/0016 433/174 |
| 2016/0038254 A1* | 2/2016 | Prestipino | A61C 1/084 433/72 |
| 2016/0143711 A1* | 5/2016 | Honig | A61C 8/005 433/174 |
| 2016/0242877 A1* | 8/2016 | Bernhard | A61C 8/005 |
| 2016/0278909 A1* | 9/2016 | Kelly | A61F 2/022 |
| 2016/0302743 A1* | 10/2016 | Casement | A61B 6/14 |
| 2017/0281474 A1* | 10/2017 | Shor | A61C 5/00 |
| 2017/0296307 A1* | 10/2017 | Simmons | A61C 8/006 |
| 2017/0312059 A1* | 11/2017 | Burger | A61C 8/005 |
| 2018/0036053 A1* | 2/2018 | Toscano | A61B 5/0492 |
| 2018/0140391 A1* | 5/2018 | Rodriguez Ciurana | A61C 8/0069 |
| 2018/0200029 A1* | 7/2018 | Schnitzspan | A61C 8/0048 |
| 2018/0200034 A1* | 7/2018 | Deville | A61C 8/005 |
| 2019/0247149 A1* | 8/2019 | Simmonds | A61C 5/70 |
| 2019/0282331 A1* | 9/2019 | Rubbert | A61C 8/0012 |
| 2019/0350683 A1* | 11/2019 | Kenealy | A61C 8/0048 |

FOREIGN PATENT DOCUMENTS

| | | |
|---|---|---|
| EP | 1446067 | 8/2004 |
| EP | 1523284 | 4/2005 |
| EP | 1628593 | 3/2006 |
| EP | 2647347 | 10/2013 |

* cited by examiner

DENTAL PROSTHESIS

BACKGROUND OF THE INVENTION

Field of the Invention

The present invention relates generally to dental prostheses. More particularly the present invention relates to a dental prosthesis having a hole, either standard or custom, through it to guide a drill, the prosthesis configured to be installed concurrently with the installation of a screw into the surrounding bone.

Description of Related Art

Generally, the installation of a dental prosthesis replicating a tooth is performed in two steps. The first step is the installation of a bone screw into a bone of a patient. This involves drilling a hole, and then setting a screw. This screw must then set for a period of time to allow the patient's body to adapt and accept the screw, and allow new bone growth in and around the screw. Only after this time period has elapsed can a replica tooth prosthesis (commonly called a "crown") be installed by connecting it to this now secure screw. Usually this connection is via an adhesive. This process requires a substantial amount of a dentist's time, leading to higher costs. Further, the waiting period after the screw is implanted is uncomfortable and difficult for the patient. Further still, the bone target for screw installation, which will be drilled, is often not uniform, and is difficult to estimate. As such, the drilling may easily be off, causing a misaligned screw, or worse.

Moreover, unguided drilling creates a number of additional difficulties such as maintaining proper drill orientation throughout the entire drilling process. Failure to do so can cause unwanted widening of the drilled hole as well as a non-straight and non-uniform hole.

Therefore, what is needed is a dental prosthesis that may be installed at the same time as the installation of the screw, and that may also aid in guiding proper placement of the drilled hole and screw therein.

SUMMARY OF THE INVENTION

The subject matter of this application may involve, in some cases, interrelated products, alternative solutions to a particular problem, and/or a plurality of different uses of a single system or article.

In one aspect, a dental prosthesis is provided. The prosthesis comprises a tooth-shaped body having a top chewing face, bottom implanting face, and side faces. The body further comprises a guide hole through its height between the top chewing face and bottom implanting face. The guide hole forms a channel through the body allowing passage and guidance of a drill bit. In operation, once the prosthesis is set in place in its implantation area, a drill may be used to drill a hole for the placement of a securing bone screw. The drill bit will be guided by the guide hole, ensuring that the drilled hole is straight and in the correct bone area.

In another aspect, a method of implanting a dental prosthesis is provided. The method begins with a pre-formed dental prosthesis having a guide hole through its height, the guide hole is sized to allow passage and guidance of a drill bit. In some embodiments, the guide hole may be custom oriented to direct the hole in a direction for best screw mounting of the particular patient. This prosthesis is set and temporarily held in place. A hole may be drilled in the bone of the patient. This drilling comprises guiding the drill bit through the guide hole of the prosthesis, which guides the drill and ensures it takes a proper path into the bone. Once the hole in the bone has been drilled, a screw may be implanted into this hole. The screw then holds the prosthesis permanently in place to the bone with part of the screw being held in the bone, and part of the screw being held in the prosthesis.

DETAILED DESCRIPTION

Figure 1A:
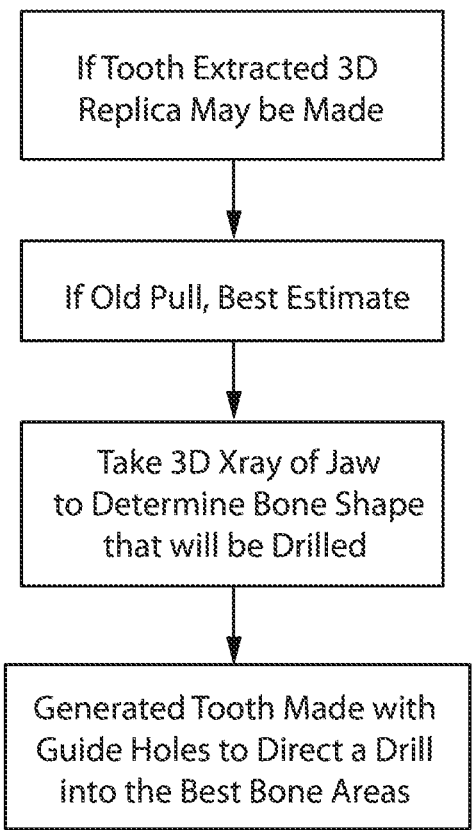
FIG. 1A provides a flow chart of an embodiment of steps involved in generating a dental prosthesis.

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

Generally, the present invention concerns a dental prosthesis configured to be installed concurrently with a bone screw to support and anchor the prosthesis. Further, the invention concerns a dental prosthesis that includes a guide for a drill to ensure proper orientation of drilling a hole in bone for subsequent screw installation. The guide hole may be formed to align the drilled hole and screw with the ideal bone installation area. Moreover, by directly attaching the screw to the prosthesis, no adhesive cement is needed, thereby eliminating problems caused by the cement including gum irritation and infection.

The dental prosthesis contemplated herein is formed to replicate a tooth it is replacing. In one embodiment, this may be a single tooth. In another embodiment, the prosthesis may cover multiple teeth. In addition to this, the prosthesis is formed having a guide hole through its height that will guide a drill bit into the bone. Once the drill bit drills a proper hole as guided by the guide hole, a screw may be inserted, anchoring the prosthesis to the bone. This guide hole may be threaded, or smooth, depending on embodiment. In one threaded embodiment, the threads may be formed directly into the prosthesis material. In another embodiment, a sleeve may contain the threads and may have the prosthesis formed around it. The sleeve may be, for example, a durable material such as titanium or the like.

As is known in the art, a screw preferably may be given a period of time to be accepted by the patient's body before it can fully support the dental prostheses (often referred to as a crown). This is because the patient's body takes time to accept the implanted screw, and grow bone around it to hold it securely in place.

The screw contemplated herein may be any shaft, threaded or otherwise, capable of being implanted securely into a bone of a patient. The screw may be configured to set into a pre-drilled hole, may be self-driven, or self tapping, among other options.

In one embodiment, to accommodate for this, allowing the present invention to be installed concurrently with the screw, at least one wing, and preferably two, will extend from the sides of the prosthesis. These wings are configured to be adhered to neighboring teeth to temporarily secure the prosthesis in place while the screw is being set. Once the screw is set and received, the wings may no longer be necessary. In varying embodiments, the wings may be removed, or may remain on the teeth.

Another embodiment allowing securing of the tooth while the screw is setting involves a retainer. The retainer may be removable connectable to adjacent existing teeth in the patient's mouth and may protect and secure the prosthesis. The retainer may be used as alternative to, or in addition to the wings.

In embodiments wherein a tooth is being extracted and will soon after be replaced with a prosthesis, a 3D model may be taken of the tooth, and then replicated such that the replacement tooth is a nearly identical replica of the original removed tooth. For example a 3D scan of a removed tooth of the patient may be taken using a computerized system. Based on this scan, the prosthesis may be generated automatically using a computer controlled system based on the scanned removed tooth. This generated replica may be formed as a crown only, or may comprise a partial or complete root for the tooth prosthesis.

In another embodiment, the present invention may be formed as an abutment having a guide hole for the screw. In this embodiment, the abutment may be installed concurrently with the screw, using the abutment to guide the screw into the appropriate bone area. This abutment may be allowed to set and, once set, a permanent crown may be installed on the abutment. In a similar embodiment, a temporary crown may be attached to the abutment at the time of installation of the screw and abutment. Once the screw has set, the temporary crown may be removed, and a permanent crown may be attached.

In embodiments wherein the tooth has been removed and the original tooth is not available, a best guess may be made to replicate the original tooth based on measurements of the installation area.

In one embodiment, a method of identifying the best area for bone drilling may include taking a 3D X-ray of the jaw or bone around the tooth. This will provide a 3D model of the bone structure around the area to be drilled, and will allow the operator to identify the path the screw will take. Based on this, the tooth may be fabricated with the guide hole to guide the drill into the bone accordingly. However, it should be understood that any method to identify the best path for the screw may be used. It should be understood that the prosthesis guide hole may be configured based on the identified best area for drilling to control angle, width, and depth, thereby limiting damage and danger that can be done when drilling and/or setting the screw.

In embodiments wherein the prosthesis is a non-molar tooth, it may be necessary to have the guide hole at least partially pass through a front of the tooth. This may be because the ideal bone area to set the screw in is at an angle to the tooth, and the tooth is too small or thin to have the screw pass through its top face. In such embodiments, the hole may be filled with a composite, forming a plug, or may have a veneer placed over it, covering the hole entirely.

Typically, after the tooth and screw have been installed in place, the guide hole of the tooth may be filled, thereby completing the prosthesis. The filling may be performed with any filling known in the art such as a composite, dental metal, or the like. In another embodiment, the filling may be performed by applying a veneer to the tooth, covering the hole. This embodiment may be particularly useful when the guide hole protrudes through a side of the tooth.

The dental prosthesis may be made of any material capable of being mounted within a mouth of the patient. Generally, the prosthesis may be any material typically used to make crowns and similar prostheses in the dental field. However, it should be understood that this invention is not limited to these materials.

In most embodiments, the prosthesis is formed as a top portion of a tooth, excluding the root that extends underneath the gums into the bone. The prosthesis may comprise a biting area on a top face configured to have shaping and facets like a human tooth. The opposing side of the prosthesis is configured to be placed into the gum and bone area of the patient. Similarly, the side faces may be sized and shaped to mimic the tooth they are replacing.

Similarly, the screw may be any material capable of being screwed into bone and set therein. Generally, the screw may be made of typical medical or dental implant material such as zirconium, titanium, or the like. However, it should be understood that this invention is not limited to these materials.

The drill contemplated herein may be any drill capable of drilling into bone tissue. Any existing dental or medical drill may be used, as well as future innovations on such drilling devices.

Turning now to FIG. 1A, a flow chart of an embodiment of a process of preparing the dental prosthesis is provided. The process may begin with a 3D replica of an extracted tooth being made. Or, if the prosthesis is for an old pull or the tooth is otherwise not available, or if a 3D replica is not desired, the prosthesis may be formed to best estimate the original tooth. A 3D X-ray of the jaw (assuming the prosthesis is going into a jaw, other bone area if the prostheses is going into the upper mouth) may be taken to determine the bone shape and identify the exact area where drilling and mounting of the screw will take place. The direction that the screw will be inserted will be determined from this X-ray. Based on the determined screw direction, the prosthesis may be generated with a guide hole configured to guide a drill inserted through the hole in the determined direction for the screw. In other embodiments, a 3D x-ray may not be required, and a direction for the screw may be estimated based on other observations such as a visual assessment, physical assessment, or other imaging methods. The guide hole may then be generated with the prosthesis based on these observations.

Figure 1B:
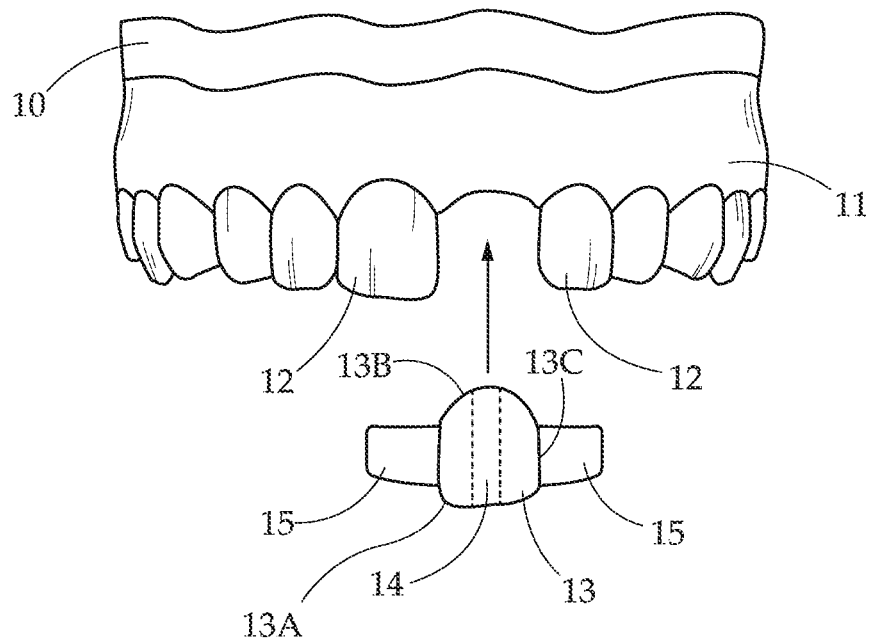
FIG. 1B provides a view of the generated prosthesis being prepared for installation.

FIG. 1B provides a view of the generated prosthesis being prepared for installation. A jaw bone 10 is shown having gums 11 covering them. Existing teeth 12 surround the implantation area. The prosthesis body 13 has a top chewing face 13A that will align with the top faces of the surrounding teeth and be configured for chewing like the original tooth it is replacing. The prosthesis further comprises a bottom implanting face 13B. This face is configured and formed to set into the gums and bone area of the patient and be seated therein. Side faces 13C of the body surround the body and define its side perimeter.

The generated prosthesis body 13 has a guide hole 14 extending through its height. This guide hole 14 is configured to guide a drill through the hole and properly into the bone 10 so that a screw (not shown) that is properly secured in the bone 10 may be implanted. The guide hole 14 is sized to closely receive a drill bit and sized to prevent the drill bit from straying off the path guided by the guide hole. As such, the guide hole, in many embodiments, may have an inner diameter or width that is the same, or only slightly bigger (0.1-1 mm) than the outer diameter or width of the drill bit. In an alternative embodiment, the guide hole 14 diameter or width may be slightly smaller than the drill bit diameter or width.

Two tabs 15 extend from either side face 13C of the prosthesis 13. These tabs will be used to secure the prosthesis 13 in place once it is set into the implantation area. The securement may be in any manner capable of holding the prosthesis 13 in place. In one embodiment, the tabs 15 may be adhered to the adjacent teeth 12.

Figure 2:
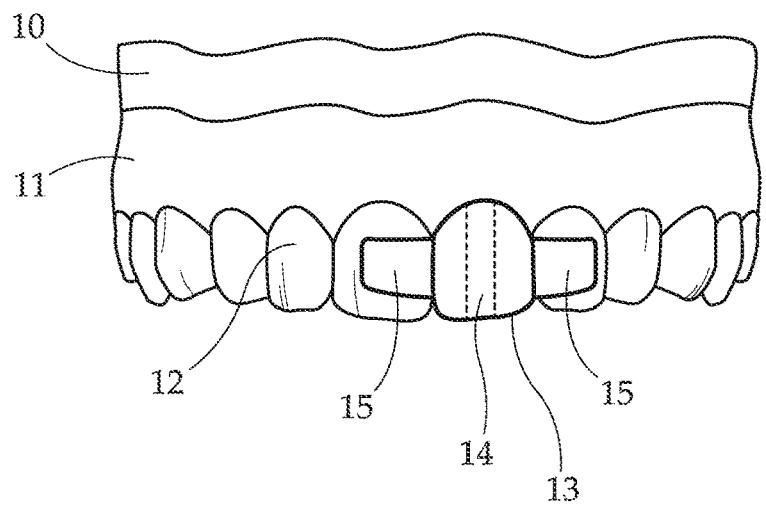
FIG. 2 provides a view of an embodiment of the dental prosthesis and implantation.

FIG. 2 shows an embodiment of the prosthesis placed in the implantation area. The prosthesis 13 is fitted between the existing teeth 12. Tabs 15 are connected to the adjacent teeth 12 and, in this embodiment, adhered thereto. Once the prosthesis 13 is properly fitted in place, the guide hole 14 will be properly aligned to guide the drill for screw placement.

Figure 3:
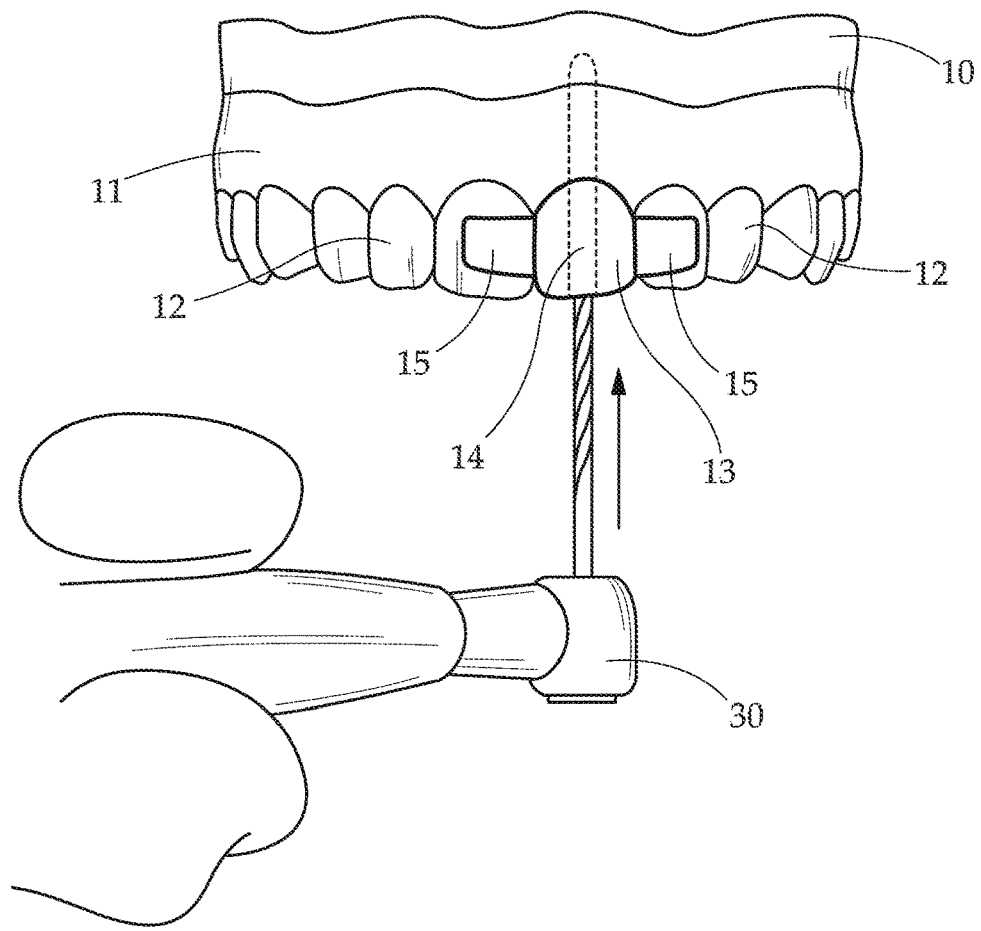
FIG. 3 provides a view of another embodiment of the dental prosthesis and implantation.

FIG. 3 provides a view of the guide hole guiding a drill. The prosthesis 13 is fitted between the existing teeth 12. Tabs 15 are connected to the adjacent teeth 12 and, in this embodiment, adhered thereto. The drill 30 and drill bit are inserted into the guide hole 14 which maintains the drill 30 in a correct orientation so that it can only drill in the direction guided by the guide hole 14. The drill is then urged into the bone 10 as shown by the directional arrow thereby drilling the hole. Once a proper depth for screw insertion has been achieved, the drilling is completed and the drill 30 may be removed.

Figure 4:
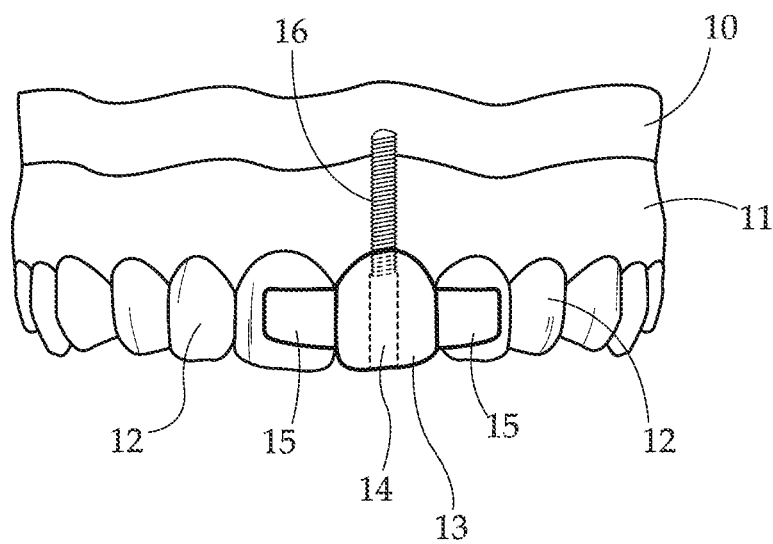
FIG. 4 provides a view of another embodiment of the dental prosthesis and implantation.

FIG. 4 provides a view showing the screw installed after drilling. After drilling is completed, screw 16 may be implanted by screwing it into the drilled hole through the guide hole 14. Once implanted, the screw 16 will hold the prosthesis 13 to the bone 10. As noted above, it takes a period of time for the screw 16 to be fully stable and accepted by bone 10. While this time period is elapsing, the prosthesis 13 is held in place by the tabs 15 attached to adjacent teeth 12.

Figure 5:
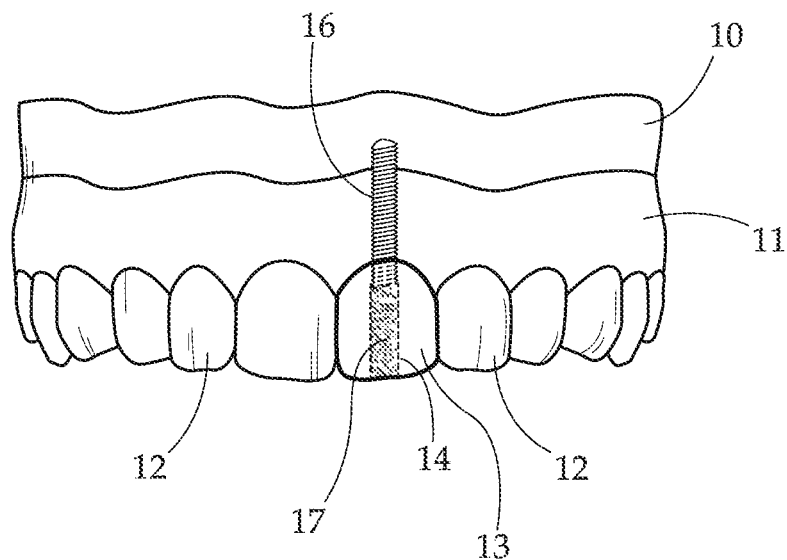
FIG. 5 provides a view of still another embodiment of the dental prosthesis and implantation.

FIG. 5 provides a view of an embodiment of the prosthesis fully installed. In this view, the screw 16 has had time to fully set, permanently holding the prosthesis 13 in place. Tabs (not shown) have been removed because once the screw has fully set, they are no longer necessary. The through hole 14 has been filled with a composite material 17 mimicking a tooth material.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

What is claimed is:

1. A method of forming and installing a dental prosthesis comprising the steps of:
    identifying a drilling path of the patient, the drilling path being projected from a dental prosthesis into a bone of the patient, the dental prosthesis comprising:
        a prosthesis body, the prosthesis being a replacement for a missing tooth, the body having a tooth-shape and formed to replicate the tooth of a patient and to be implanted into a mouth of the patient, the body comprising a top chewing face, a bottom implanting face, and side faces;
    wherein the body forms a guide hole from the top face to the bottom face, the guide hole forming a channel sized to guide a drill, and sized to closely receive a drill bit to prevent the drill bit from straying off a path guided by the guide hole during a drilling operation;
    a screw, the screw attached to the prosthesis body and engaged with threads within the guide hole, and the screw extending beyond the bottom implanting face; and
    a filling within the guide hole closing an opening of the guide hole at the top chewing face;
    forming the dental prosthesis, the guide hole being formed to align with the drilling path when the prosthesis bottom implanting face is positioned on an implantation area;
    positioning the dental prosthesis in the implantation area of the patient;
    drilling a screw hole in the bone of the patient, the hole configured for the receipt of a bone screw, the drilling comprising guiding a drill bit through the guide hole and into the bone; and
    implanting a screw into the screw hole through the guide hole, the screw remaining partially in the guide hole and partially in the screw hole.

2. The method of claim 1 further comprising the step of adhering a tab extending from the side face of the prosthesis to an adjacent tooth once the prosthesis has been positioned in the implantation area.

3. The method of claim 2 further comprising removing the tab adhered to the adjacent tooth and the prosthesis after the screw has set in the bone.

4. The method of claim 1 wherein the step of identifying the drilling path comprises taking a three-dimensional X-ray, and analyzing the X-ray to identify the drilling path in the bone of the patient.

5. The method of claim 1 further comprising the step of filling the guide hole with a composite once the screw is implanted.

6. The method of claim 1 wherein the step of drilling comprises guiding the drill bit through the guide hole, the guide hole being sized to closely receive the drill bit and sized to prevent the drill bit from straying off the path guided by the guide hole.

7. The method of claim 1 wherein the dental prosthesis further comprising a tab extending from one side face of the body, the tab configured to be adhered to an adjacent tooth.

8. The method of claim 1 wherein the dental prosthesis further comprising a plurality of tabs, each tab extending from one side face of the body, each of the plurality of tabs being configured to be adhered to an adjacent tooth.

9. The method of claim 8 wherein the tab is adhered to the adjacent tooth, and wherein the body is mounted to a bone of the patient by a screw, the screw positioned at least partially in the guide hole.

10. A method of fixedly implanting a dental prosthesis comprising the steps of:
    setting a dental prosthesis in an implantation area of a patient, the dental prosthesis having a guide hole through its height, the dental prosthesis having a top chewing face and a bottom implanting face, with the guide hole extending between the top chewing face and bottom implanting face, the guide hole sized to allow the passage of a drill bit;

drilling a screw hole in a bone of the patient, the drilling comprising guiding the drill bit through the guide hole, the guide hole guiding the drill bit as it drills into the bone; and implanting a screw into the screw hole through the guide hole, the screw anchoring the prosthesis to the bone and remaining partially in the guide hole and partially in the screw hole, the implanting step permanently holding the prosthesis fixedly in place;

filling the guide hole with a filling once the screw is implanted, the filling closing an opening of the guide hole on the top chewing face; and wherein the step of drilling comprises guiding the drill bit through the guide hole, the guide hole being sized to closely receive the drill bit and sized to prevent the drill bit from straying off a path guided by the guide hole.

11. The method of implanting a dental prosthesis of claim 10 further comprising the steps of:

identifying a drilling path of the patient, the drilling path being projected from the prosthesis into a bone of the patient; and forming the dental prosthesis, the guide hole being formed to align with the drilling path.

12. The method of implanting a dental prosthesis of claim 11 wherein the step of identifying the drilling path comprises taking a three-dimensional X-ray, and analyzing the X-ray to identify the drilling path in the bone of the patient.

13. The method of implanting a dental prosthesis of claim 11 wherein the step of forming the dental prosthesis comprises scanning a removed tooth of the patient using a computer; and generating the prosthesis automatically using a computer controlled system based on the scanned removed tooth.

14. The method of implanting a dental prosthesis of claim 10 further comprising the step of adhering a tab extending from the side face of the prosthesis to an adjacent tooth once the prosthesis has been positioned in the implantation area.

15. The method of implanting a dental prosthesis of claim 14 removing the tab adhered to the adjacent tooth and the prosthesis after the screw has set in the bone.

* * * * *